United States Patent [19]

Kramer et al.

[11] 4,307,243
[45] Dec. 22, 1981

[54] PROCESS OF PREPARING DIHALOVINYL COMPOUNDS

[75] Inventors: Petrus A. Kramer, Amsterdam, Netherlands; Pieter A. Verbrugge, Houston, Tex.

[73] Assignee: Shell Oil Company, Houston, Tex.

[21] Appl. No.: 134,022

[22] Filed: Mar. 25, 1980

[30] Foreign Application Priority Data

Mar. 27, 1979 [GB] United Kingdom ............... 10662/79

[51] Int. Cl.³ ..................... C07C 67/307; C07C 41/48
[52] U.S. Cl. ................................. 560/124; 260/456 R; 260/463; 260/941; 260/946; 260/950; 260/957; 260/960; 568/346; 568/347; 568/591; 570/216; 570/218
[58] Field of Search ............... 260/648 R, 654 R, 655, 260/656 R, 651 R; 560/124; 568/591, 346, 347

[56] References Cited

U.S. PATENT DOCUMENTS 4,018,838  4/1977  Cleave ........................... 260/654 R

FOREIGN PATENT DOCUMENTS 52-33652  3/1977  Japan ................................. 560/124
52-73842  6/1977  Japan ................................. 562/506
52-73843  6/1977  Japan ................................. 562/506

OTHER PUBLICATIONS

Stanley, J. Am. Chem. Soc., 81 pp. 1600–1602 (1959).
March, "Advanced Organic Chemistry", 2nd Ed., pp. 944–945 (1977).
Farkas, Coll. Czech. Chem. Commun., 24 pp. 2230–2236 (1959).

*Primary Examiner*—Natalie Trousof
*Assistant Examiner*—Michael Shippen

[57] ABSTRACT

Conversion of esters $(R^1)(R^2)C(C\ Hal_3)OX$, X being-P $Hal_2$, $—C(O)OR^3$ or

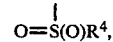

$R^1$, $R^3$ and $R^4$ being optionally substituted hydrocarbyl groups and $R^2$ methyl or hydrogen, with zinc in acetic acid gives a very high yield of a dihalovinyl compound $(R^1)(R^2)C\!=\!C\ Hal_2$, e.g., of the ethyl ester of the parent acid of pyrethroid insecticides.

12 Claims, No Drawings

PROCESS OF PREPARING DIHALOVINYL COMPOUNDS

BACKGROUND OF THE INVENTION

1. Field of the Invention

This invention relates to a process of preparing dihalovinyl compounds from certain carbonates, dihalophosphates and sulphonates.

2. Description of the Prior Art

According to Coll. Czech. Chem. Comm. 24 (1959), 2230–2236, 3-methyl-1-trichloromethyl-2-butenyl acetate can be converted with zinc and acetic acid into 1,1-dichloro-4-methyl-1,3-pentadiene and 1,1-dichloro-4-methyl-1,4-pentadiene, respectively, but these two compounds of formula I are obtained in a moderate yield. The Applicants have tried to convert other 1-trihalomethyl-2-hydrocarbyl acetates with zinc and acetic acid, but always obtained the corresponding compounds of formula I in moderate yields only.

SUMMARY OF THE INVENTION

It has now been found that 1-trihalomethyl-2-hydrocarbyl carbonates, dihalophosphites and sulphonates afford the compounds of formula I in a much higher yield than the 1-trihalomethyl-2-hydrocarbyl acetates.

Accordingly, the invention provides a process for the preparation of a compound of the general formula:

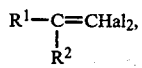

$$R^1-\underset{R^2}{\underset{|}{C}}=CHal_2, \qquad (I)$$

wherein $R^1$ represents an optionally substituted hydrocarbyl group, $R^2$ a methyl group or a hydrogen atom or $R^1$ and $R^2$, together with the carbon atom to which they are attached jointly form a cycloalkylidene group, and each Hal stands for a chlorine or bromine atom, which process comprises contacting a trihalomethyl compound of the general formula:

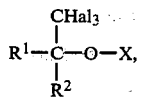

$$\underset{R^2}{\overset{CHal_3}{\underset{|}{R^1-C-O-X,}}} \qquad (II)$$

wherein $R^1$, $R^2$ and Hal have the same meaning as in formula I and X represents a group $-PQ_2$,

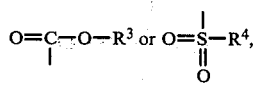

$$O=C-O-R^3 \text{ or } O=\underset{\underset{O}{\|}}{S}-R^4,$$

wherein Q represents a halogen atom and $R^3$ and $R^4$ both represent an optionally substituted hydrocarbyl group, with zinc and an alkanoic acid with fewer than 5 carbon atoms per molecule. The process according to the invention may be carried out, for example, in the presence of valeric, isobutyric, butyric or propionic acid, but preference is given to acetic acid. The zinc is suitably applied as powdered zinc, for example zinc dust. The molar ratio of zinc to the compound of formula II is not critical and may vary within a wide range, suitably between 1 and 10 and preferably between 1 and 5. The process is suitably carried out at a temperature in the range of from 10° to 100° C., for example from 15° to 50° C. Ambient temperature, for example in the range of from 20° to 35° C., is usually very suitable. If desired, the process may be carried out in the presence of a solvent, for example an ether, such as diethyl ether.

Preferred compounds of formula II are those in which $R^1$ represents an optionally substituted cyclopropyl group, particularly an optionally 3-substituted 2,2-dimethylcyclopropyl group, because such carbonyl compounds are intermediates in the preparation of synthetic pyrethroids. Among these compounds those in which $R^1$ represents a 2-alkoxycarbonyl-3,3-dimethylcyclopropyl group, in which the alkoxy group has fewer than five carbon atoms, are preferred. This alkoxy group is preferably a methoxy or an ethoxy group; methoxy groups are most preferred. Other preferred compounds of formula II are those in which $R^1$ represents a 2-(2,2-dimethoxyethyl)-3,3-dimethylcyclopropyl group.

Very good results have been obtained with compounds of formula II in which $R^1$ represents an optionally substituted alkyl group, particularly with fewer than ten carbon atoms. Examples of such alkyl groups are isopropyl, ethyl and methyl groups. Very suitable are compounds of formula II in which $R^1$ represents a cyclopropyl-substituted methyl group, particularly a 2,2-dimethyl-3-(2-oxypropyl)cyclopropylmethyl group.

Further examples of compounds of formula II are those in which $R^1$ represents an optionally substituted cyclohexyl group, for example an unsubstituted cyclohexyl group, or an optionally substituted aromatic group, such as an optionally substituted phenyl group, for example an unsubstituted phenyl group.

Some compounds mentioned hereinafter have been given a number; these numbers are also indicated below the structural formulae of these compounds on the attached drawing.

A preferred compound of formula II is: methyl 2,2,2-trichloro-1-(2,2-dimethyl-3-methoxycarbonylcyclopropyl)ethyl carbonate (compound 1).

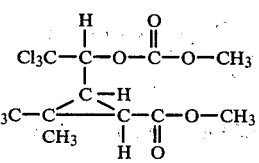

Other examples of compounds of formula II are: methyl 2,2,2-trichloro-1-[2-(2,2-dimethoxyethyl)-3,3-dimethylcyclopropyl]ethyl carbonate (compound 3).

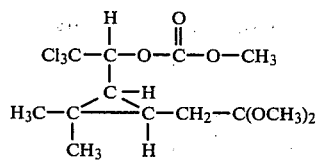

methyl 3-[2,2-dimethyl-3-(2-oxopropyl)cyclopropyl]-1,1,1-trichloro-2-propyl carbonate (compound 4),

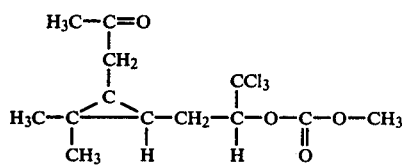

methyl 2,2,2-trichloroethyl-1-cyclohexylethyl carbonate (compound 5),

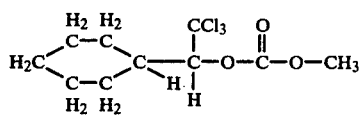

methyl 1,1,1-trichloro-3-methyl-2-butyl carbonate (compound 6),

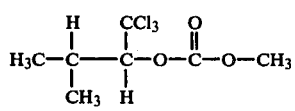

methyl 1,1,1-tribromo-3-methyl-2-butyl carbonate (compound 7), methyl 1,1,1-trichloro-2-octyl carbonate (compound 8),

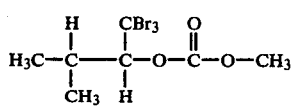

methyl 1-trichloromethylcyclohexyl carbonate (compound 9),

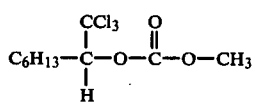

methyl 1,1,1-trichloro-2-methyl-2-butyl carbonate (compound 10),

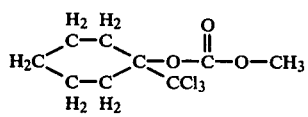

methyl 1,1,1-trichloro-2-methyl-2-propyl carbonate (compound 11).

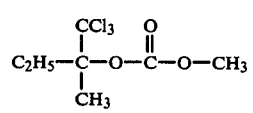

$R^4$ in the group

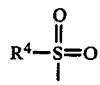

preferably represents an optionally substituted alkyl group, particularly one with fewer than 10 carbon atoms; methyl groups are most preferred. Examples of such compounds of formula II are methyl 1,1,1-trichloro-3-methyl-2-butyl sulphonate (compound 12),

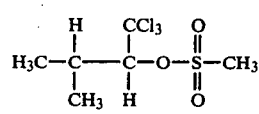

and methyl 1,1,1-tribromo-3-methyl-2-butyl sulphonate (compound 13).

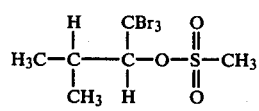

Q in the group —$PQ_2$ preferably represents a chlorine or bromine atom. A preferred compound of formula II is 2,2,2-trichloro-1-(2,2-dimethyl-3-methoxycarbonyl-cyclopropyl)ethyl dichlorophosphite (compound 2).

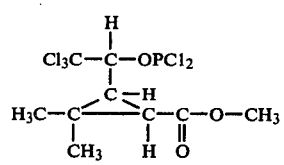

Other examples of compounds of formula II are: 1,1,1-tribromo-3-methyl-2-butyl dichlorophosphite (compound 14),

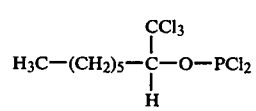

1,1,1-trichloro-2-octyl dichlorophosphite (compound 15)

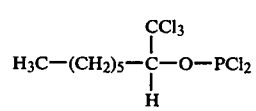

and 1,1,1-trichloro-2-octyl dibromophosphite (compound 16).

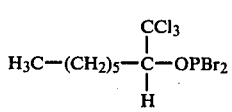

The compounds of the general formula II can be obtained as described in British patent application No. 79/10661, filed Mar. 27, 1979, and a concurrently filed U.S. application Ser. No. 133,773, now U.S. Pat. No. 4,285,882 based thereon namely by reacting a carbonate of the general formula

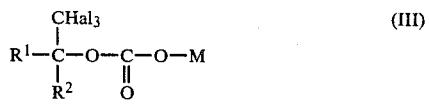

wherein $R^1$, $R^2$ and Hal have the same meaning as in formula II and M represents an alkali metal atom, with (a) an alkylating agent to give a compound of formula II in which X represents the group $-C(O)OR^3$, (b) a hydrocarbylsulphonylating agent to give a compound of the general formula II in which X represents the group

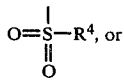

(c) a phosphorus trihalide to give a compound of formula II in which X represents the group $-PQ_2$.

The compounds of formula III can be prepared as described in British patent application No. 79/10661, filed Mar. 27, 1979, namely by reacting a carbonyl compound of the general formula:

wherein $R^1$ and $R^2$ have the same meaning as in formula III, with a trihaloacetate of the general formula:

wherein M and Hal have the same meaning as in formula III, in the presence of a highly polar, aprotic, inert solvent.

Compounds of the general formula I in which $R^1$ represents a substituted cyclopropyl group, such as 2-(2,2-dimethoxyethyl)-3,3-dimethylcyclopropyl group, and $R^2$ a hydrogen atom or a methyl group are intermediates in the preparation of 3-aryloxybenzyl esters of substituted 2,2-dihalovinylcyclopropanecarboxylic acids, for example, as described in allowed U.S. Ser. No. 55,855 now U.S. Pat. Nos. 4,222,964 and 55,858, by hydrolyzing the dihalovinylcyclopropylethanal dimethylacetal to the corresponding free ethanal compound followed by treatment with an alkanoic acid anhydride, e.g., in the presence of an amine, to yield a dihalovinylcyclopropylvinyl alkanoate, which when ozonized followed by oxidative decomposition, yields the free dihalovinylcyclopropanecarboxylic acid for esterification. These esters—which are also called "synthetic pyrethroids"—have exceptionally good insecticidal properties while possessing a very low mammalian toxicity (see U.S. Pat. No. 4,024,163). This combination of properties makes them of considerable interest to the agrochemical industry and much effort has been expended in finding economic routes for their preparation.

EXAMPLES

The following examples further illustrate the invention. Yields and purities were determined by nuclear magnetic resonance (NMR) spectroscopy.

EXAMPLE I

Preparation of 1,1-dichloro-3-methyl-1-butene.

An NMR tube was charged with a solution of sodium trichloroacetate (1.1 mmol) in N,N-dimethylformamide (0.8 ml) and then with isobutyraldehyde (0.95 mmol). After 30 minutes' shaking the tube contained a thick slurry, a precipitate of sodium 1,1,1-trichloro-3-methyl-2-butyl carbonate being present, and 90% of the isobutyraldehyde had been converted, with a selectivity to this carbonate of 75%. Then, dimethyl sulphate (0.95 mmol) was added and shaking was continued for 16 hours. Subsequently, 36% w aqueous hydrochloric acid (0.3 ml) was added and the mixture obtained was poured out into water (50 ml). The mixture thus formed was extracted with n-pentane (50 ml), the extract phase was washed with three 15-ml portions of water and with a saturated aqueous solution of sodium hydrogen carbonate (10 ml), the washed liquid was dried over anhydrous magnesium sulphate and the n-pentane was evaporated at sub-atmospheric pressure from the dried liquid to leave an oily residue (0.12 g) having a content of methyl 1,1,1-trichloro-3-methyl-2-butyl carbonate (compound 6) of 88%, the yield thereof being 50%.

Then, the contents of a 10-ml flask charged with methyl 1,1,1-trichloro-3-methyl-2-butyl carbonate (0.90 mmol) prepared as described above, zinc powder (1.5 mmol), diethyl ether (5 ml) and glacial acetic acid (1 ml) was stirred at 20° C. for 45 min. The title compound was obtained in quantitative yield.

EXAMPLE II

Preparation of 1,1-dibromo-3-methyl-1-butene.

The contents of a 10-ml flask charged with 1,1,1-tribromo-3-methyl-2-butanol (0.92 mmol) and phosphorus trichloride (1.0 mmol) were stirred at 40° C. for 1.5 hours. Then, the excess of phosphorus trichloride was evaporated at sub-atmospheric pressure leaving a residue containing 1,1,1-tribromo-3-methyl-2-butyl dichlorophosphite (compound 14). Diethyl ether (5 ml). glacial acetic acid (1 ml) and powdered zinc (1.5 mmol) were added to the residue and the mixture obtained was stirred at 20° C. for 20 min. The conversion of the 1,1,1-tribromo-3-methyl-2-butanol was 100%, with a selectivity to the title compound of 97%.

Comparative experiment

The contents of a 50-ml flask charged with 1,1,1-tribromo-3-methyl-2-butyl acetate (3.0 mmol), diethyl ether (15 ml), glacial acetic acid (3 ml) and zinc powder (4.6 mmol) were stirred at 20° C. for 20 min. At the end of this period the acetate was fully converted, with a selectivity to the title compound of Example II of only 38%.

EXAMPLE III

Preparation of 1,1-dichloro-1-octene

An NMR tube was charged with n-heptanal (0.69 mmol), potassium trichloroacetate (0.29 mmol) and N,N-dimethylformamide (0.4 ml). After 35 minutes' standing—when the reaction mixture contained potassium 1,1,1-trichloro-2-octyl carbonate—36% w aqueous hydrochloric acid (0.08 ml) was added. The mixture obtained was diluted with deuterochloroform (0.4 ml) and the diluted solution was washed with three portions of water (each of 0.5 ml). The washed solution was dried over anhydrous magnesium sulphate and the solvent was evaporated from the dried solution to leave a residue containing 1,1,1-trichloro-2-octanol; the conversion of n-heptanal was 87%, with a selectivity to 1,1,1-trichloro-2-octanol of 95%.

Then, the contents of a 10-ml flask charged with 1,1,1-trichloro-2-octanol (0.86 mmol) prepared as described above, and phosphorus trichloride (1.0 mmol) were stirred at 40° C. for 1.25 hours. At the end of this period, the excess of phosphorus trichloride was evaporated at sub-atmospheric pressure. The residue contained 1,1,1-trichloro-2-octyl dichlorophosphite (compound 15) and was dissolved in diethyl ether (5 ml) and glacial acetic acid (1 ml). After addition of zinc powder (3.1 mmol) the mixture was stirred under reflux for 1.5 hours. The excess of zinc was filtered off, the filtrate was diluted with n-pentane (10 ml), the diluted solution was washed with water (10 ml), 5% w aqueous hydrochloric acid (10 ml) and a saturated aqueous solution of sodium hydrogen carbonate (5 ml), the washed solution was dried over anhydrous magnesium sulphate and the solvent was evaporated at sub-atmospheric pressure to leave a residue (0.11 g) of which the content of the title compound was 94%. The conversion of the dichlorophosphite was 100%, with a selectivity to the title compound of more than 80%.

EXAMPLE IV

Preparation of methyl 2-(2,2-dichlorovinyl)-3,3-dimethylcyclopropanecarboxylate.

Methyl cis-2-formyl-3,3-dimethylcyclopropanecarboxylate (6.0 mmol) was added with stirring to a solution of sodium trichloroacetate (6.6 mmol) in N,N-dimethylformamide (3.2 ml) present in a 25-ml flask. After 15 minutes' stirring the conversion of the starting carboxylate was 97%, with a selectivity to sodium 2,2,2-trichloro-1-(2,2-dimethyl-3-methoxycarbonylcyclopropyl)ethyl carbonate of more than 90%. Then, 36% w aqueous hydrochloric acid (0.6 ml) and water (50 ml) were added and the mixture obtained was extracted with three 15-ml portions of n-pentane. The combined extract phases were washed with water (20 ml) and a saturated aqueous solution of sodium hydrogen carbonate (20 ml). The washed liquid was dried over anhydrous magnesium sulphate and the n-pentane was evaporated at sub-atmospheric pressure from the dried liquid to give a residue (1.47 g) having a content of methyl 2-(2,2,2-trichloro-1-hydroxyethyl)-3,3-dimethylcyclopropanecarboxylate of 95%, the yield thereof being 85%. The contents of a flask charged with the latter compound (0.73 mmol) and phosphorus trichloride (0.80 mmol) were stirred at 40° C. for 45 min. At the end of this period phosphorus trichloride was evaporated at sub-atmospheric pressure. The residue contained 2,2,2-trichloro-1-(2,2-dimethyl-3-methoxycarbonylcyclopropyl)ethyl dichlorophosphite (compound 2) and was dissolved in diethyl ether (5 ml) and glacial acetic acid (1 ml). After addition of zinc powder (1.5 mmol) the mixture was stirred under reflux for 1.5 hours (about 40° C.). At the end of this period the conversion of the dichlorophosphite was 92%, with a selectivity to the title compound of 79%. The excess of zinc was filtered off, the filtrate was diluted with n-pentane (30 ml), the diluted solution was washed with three portions of 15 ml water and one portion of a saturated aqueous solution of sodium hydrogen carbonate (10 ml), the washed solution was dried over anhydrous magnesium sulphate and the solvent was evaporated from the dried solution to give a residue of the title compound. The cis content of this compound was 60%.

EXAMPLE V

Preparation of 1,1-dibromo-3-methyl-1-butene.

The contents of a 10 ml flask charged with 1,1,1-tribromo-3-methyl-2-butanol (1.7 mmol), mesyl chloride (1.9 mmol) and pyridine (6 ml) were stirred at 20° C. for 16 hours. Then, the reaction mixture was poured out into water (50 ml), then extracted with three 15 ml-portions of dichloromethane, the combined extract phases were washed with 15 ml 36% (w) aqueous hydrochloric acid, dried over anhydrous magnesium sulphate and the solvent was evaporated from the dried liquid to leave a residue (0.9 g) of methyl 1,1,1-tribromo-3-methyl-2-butyl sulphonate (compound 13). The contents of a 10-ml flask charged with this sulphonate (0.50 mmol), zinc powder (0.75 mmol), diethyl ether (2.5 ml) and glacial acetic acid (0.5 ml) were stirred at 20° C. for 30 min. The sulphonate was fully converted, with a selectivity to the title compound of 82%.

We claim:

1. A process for the preparation of a compound of the formula I

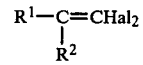

wherein $R^1$ represents a 2-(2,2-dimethoxyethyl)-3,3-dimethylcyclopropyl group, or a 2,2-dimethyl-3-alkoxycarbonylcyclopropyl) group in which the alkoxy group has fewer than five carbon atoms, $R^2$ a hydrogen atom and each Hal stands for a chlorine atom, which comprises contacting a trihalomethyl compound of the formula II

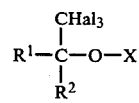

wherein $R^1$, $R^2$ and Hal have the same meaning as in formula I and X represents a group —$PQ_2$,

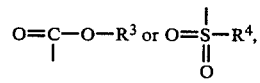

wherein Q represents a halogen atom and $R^3$ and $R^4$ both represent an alkyl group with fewer than ten carbon atoms with zinc and an alkanoic acid with fewer than 5 carbon atoms per molecule.

2. A process according to claim 1, in which $R^1$ represents a 2-alkoxycarbonyl-3,3-dimethylcyclopropyl group in which the alkoxy group has fewer than five carbon atoms.

3. A process according to claim 2, in which $R^1$ represents a 2-methoxycarbonyl-3,3-dimethylcyclopropyl group.

4. A process according to claim 1, in which $R^1$ represents a 2-(2,2-dimethoxyethyl)-3,3-dimethylcyclopropyl group.

5. A process according to claim 1 in which each of the two Q atoms in the group —PQ$_2$ is a chlorine or bromine atom.

6. A process according to claim 1, in which R$^3$ and R$^4$ both represent a methyl group.

7. A process according to claim 6, in which the compound of formula II is methyl 2,2,2-trichloro-1-(2,2-dimethyl-3-methoxycarbonylcyclopropyl)ethyl carbonate.

8. A process according to claim 5, in which the compound of formula II is 2,2,2-trichloro-1-(2,2-dimethyl-3-methoxycarbonylcyclopropyl)ethyl dichlorophosphite.

9. A process according to claim 1 in which the alkanoic acid is acetic acid.

10. A process according to claim 1 in which the zinc is powdered zinc.

11. A process according to claim 10 in which the zinc is used in an amount of from 1 to 5 mol per mol of compound of formula II.

12. A process according to claim 1 which is carried out at a temperature in the range of from 10° C. to 100° C.

* * * * *